(12) United States Patent
Lin et al.

(10) Patent No.: US 6,533,813 B1
(45) Date of Patent: Mar. 18, 2003

(54) INTRAOCULAR LENS THAT MAY ACCOMMODATE AUTOMATICALLY

(76) Inventors: Chwen Yih Lin, 8F., No. 334-1, Jong Jeng Rd., Baan Chyau City, Taipei Hsien (TW); Ray Jui-Fang Tsai, 8F., No. 334-1, Jong Jeng Rd., Baan Chyau City, Taipei Hsien (TW)

( * ) Notice: Subject to any disclaimer, the term of this patent is extended or adjusted under 35 U.S.C. 154(b) by 25 days.

(21) Appl. No.: 09/949,227

(22) Filed: Sep. 7, 2001

(51) Int. Cl.⁷ .................................................. A61F 2/16
(52) U.S. Cl. ..................... 623/6.37; 623/6.22; 623/6.41
(58) Field of Search ............................. 623/6.37–6.41, 623/6.43–6.46, 6.22

(56) References Cited

U.S. PATENT DOCUMENTS

| | | | |
|---|---|---|---|
| 5,002,571 A | * | 3/1991 | O'Donnell, Jr. et al. ... 623/6.11 |
| 5,108,429 A | * | 4/1992 | Wiley ........................ 623/6.22 |
| 5,326,347 A | * | 7/1994 | Cumming .................. 623/6.38 |
| 5,800,533 A | * | 9/1998 | Eggleston et al. ......... 623/6.39 |
| 6,096,078 A | * | 8/2000 | McDonald .................. 623/6.22 |
| 6,443,984 B1 | * | 9/2002 | Jahn et al. .................. 623/6.22 |

* cited by examiner

*Primary Examiner*—David H. Willse
*Assistant Examiner*—Suzette J. Jackson
(74) *Attorney, Agent, or Firm*—Pro-Techtor International Services

(57) ABSTRACT

The present invention is to provide an intraocular lens that may accommodate automatically, including a central optic having an anterior optic connected with the stroke cylinder, a posterior optic connected with the outer core which is connected with the stroke cylinder, thereby enclosing the central optic in an inner periphery. Thus, by change of the inclined angle of the user, or by variation of the external magnetic field, the push force that is exerted on the central optic of the intraocular lens may be regulated, so as to actively control the position of the central optic of the intraocular lens, so that the user may actively control and regulate the refractive power of the eyeball that is implanted with the intraocular lens.

13 Claims, 8 Drawing Sheets

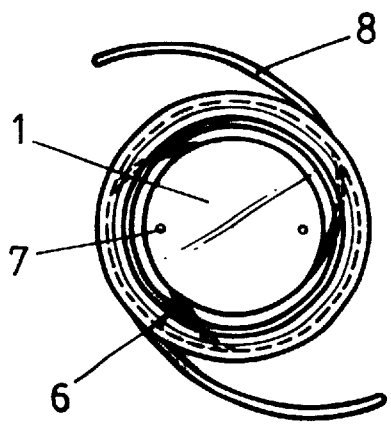 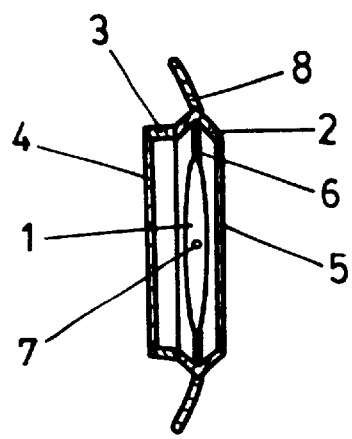
FIG.4  FIG.5
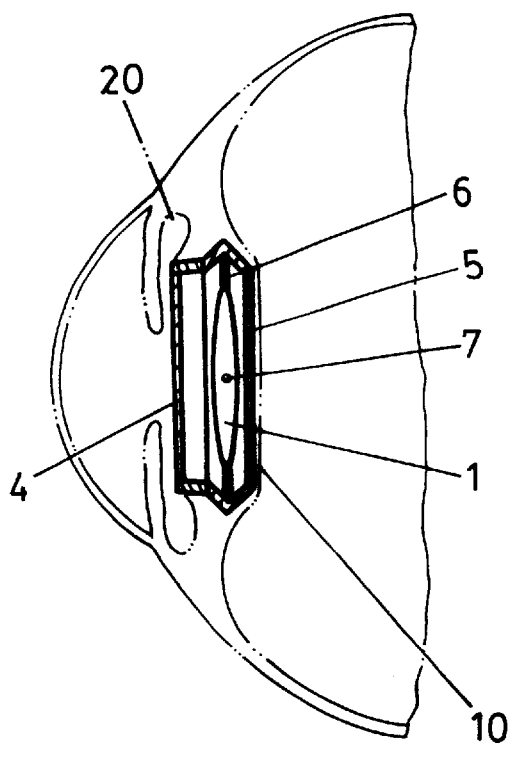 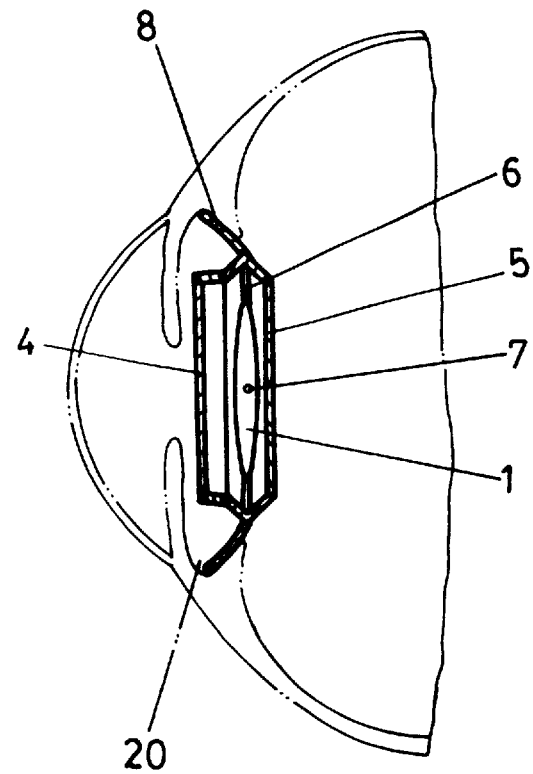
FIG.6  FIG.7

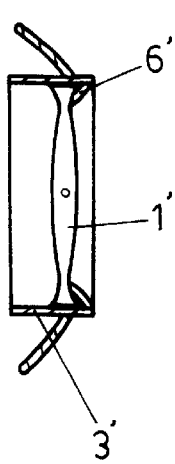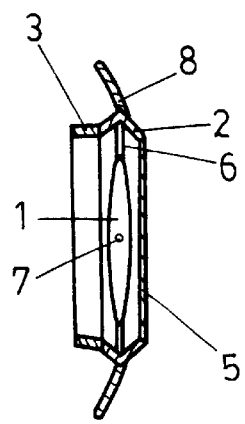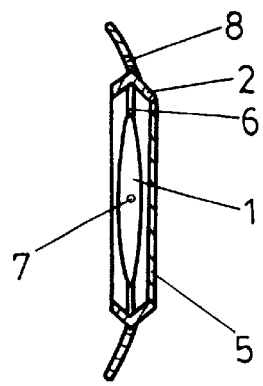
FIG.12　　　FIG.13　　　FIG.14
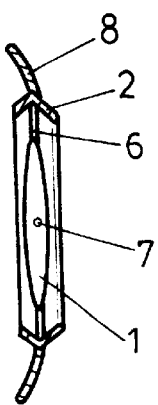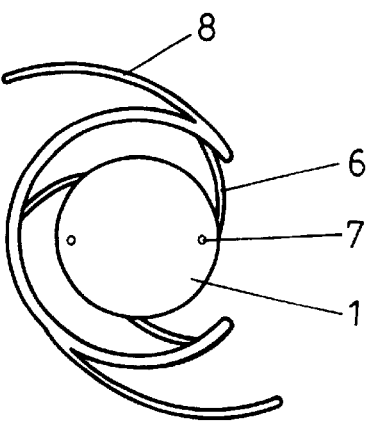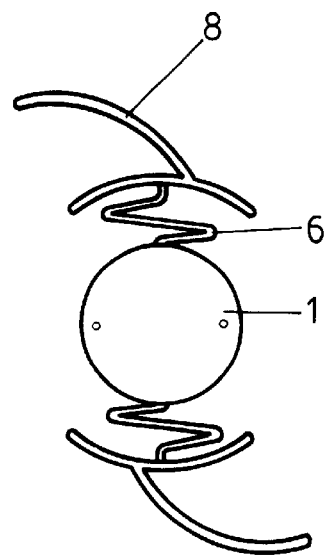
FIG.15　　　FIG.16　　　FIG.17
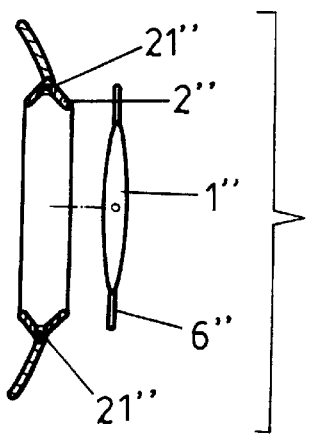
FIG.18

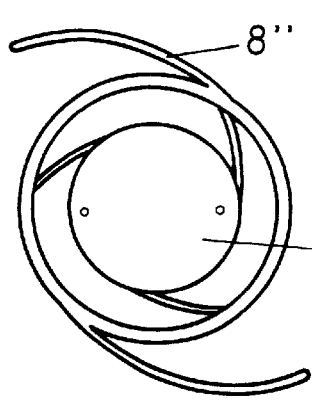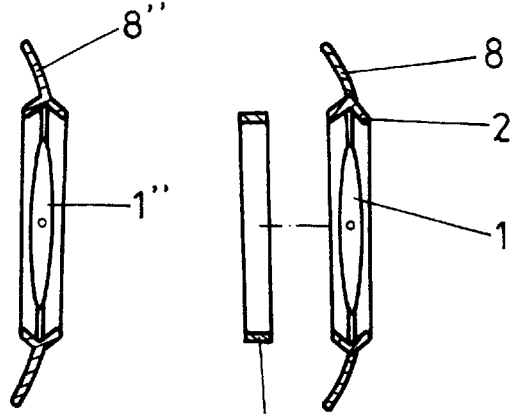
FIG.19   FIG.20   FIG.21
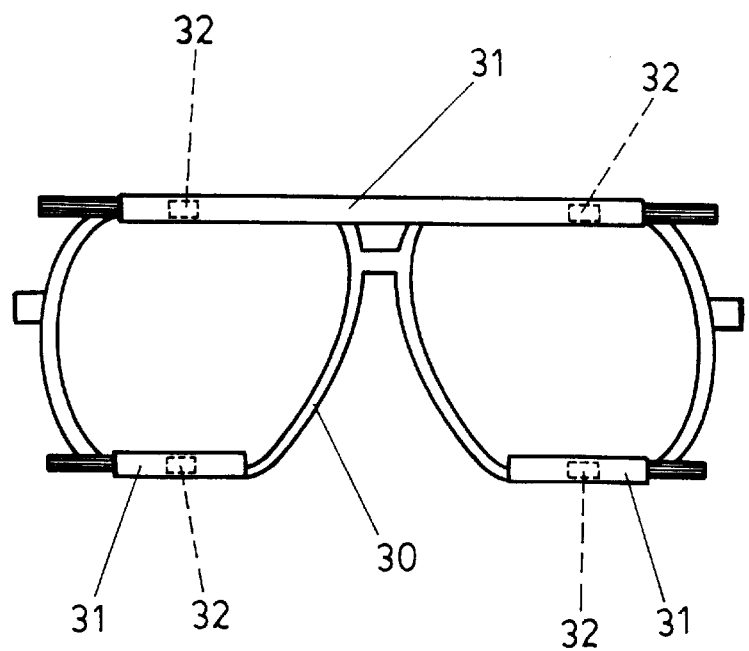
FIG.22

INTRAOCULAR LENS THAT MAY ACCOMMODATE AUTOMATICALLY

BACKGROUND OF THE INVENTION

1. Field of the Invention

The present invention relates to an intraocular lens that may accommodate automatically, and more particularly to an intraocular lens that may accommodate automatically, wherein the position of the central optic of the intraocular lens in the eyeball may be adjusted so as to change the entire refractive power of the eyeball.

2. Description of the Related Art

Usually, an intraocular lens may be used to replace the original crystalline lens when being aged or diseased. The intraocular lens may be mounted into the capsular bag of the patient. If the capsular bag is not complete, the intraocular lens may be mounted in the ciliary sulcus of the patient. However, the intraocular lens of prior art has a constant focus, so that it cannot accommodate automatically.

A conventional intraocular lens 100 in accordance with the prior art shown in FIG. 1 comprises a central optic 101, and two haptics 102 connect with the central optic 101.

As shown in FIG. 2, the conventional intraocular lens 100 is mounted in the capsular bag 200. However, the anterior chamber distance (ACD) is fixed, and the refractive power thereof cannot be adjusted.

As shown in FIG. 3, the conventional intraocular lens 100 is mounted in the ciliary sulcus 300 when the capsular bag 200 is not complete. The two haptics 102 of the conventional intraocular lens 100 are settled on the ciliary sulcus 300. However, the anterior chamber distance (ACD) is fixed, and the refractive power thereof cannot be adjusted.

There are many ways to achieve the accommodating need of human eye after cataract extraction. The first is implantation of multifocal lens, which provide many different focal areas in a lens it self. The U.S. Pat. Nos. 4,666,446, 4,710,193, 4,759,762, 5,225,858, 5,326,348, 5,507,806 are of category of multifocal design. This category of multifocal design is a compromised way of accommodation, they are not voluntary and different areas of blurred image hamper the visual field and the light amount is decreased.

The second is using a small aperture to increase the depth of field. Which is disclosed by U.S. Pat. No. 4,759,762. This method is compromised by the decreased light transmission amount and loss of visual field.

The third method is a group of designs of intraocular lens, which are directly driven or indirectly activated by the contraction of ciliary muscle. The U.S. Pat. Nos. 4,842,601, 4,888,012, 4,892,543, 4,932,966, 4,944,082, 5,476,514, 5,578,081, 5,607,472, 5,843,188, 6,197,059 B1 are of this category. This category of designs have many problems which still under investigation. The most doubtful problem is the effectiveness and the stability of the mechanical attachment of lens with the ciliary muscle.

The others, as in U.S. Pat. No. 6,200,342 B1 is an Intraocular lens which change power by pupil contraction. The U.S. Pat. Nos. 5,108,429, 5,171,266, 5,203,788, 5,800, 533 are a series of intraocular lens designs, which can fine adjusting the power by micro motor or by electromagnetic means. These designs are not for accommodating needs of human eye and the mechanical arrangement are quite different with the present invention. The present invention is an intraocular lens, which can change the position along the visual axis by will and still eliminate the need of interaction with ciliary muscle. The fixation of this invention into human eye is quite the same with the tremendous successfully used classical fixed focal intraocular lenses. So the present invention has many advantages compared with the prior art of this field.

SUMMARY OF THE INVENTION

The present invention is to provide an intraocular lens wherein the position of the central optic at the visual axis may be changed by control of the user.

The primary objective of the present invention is to provide an intraocular lens that may accommodate automatically, including a central optic having an anterior optic connected with the stroke cylinder, a posterior optic connected with the outer core which is connected with the stroke cylinder, thereby enclosing the central optic in an inner periphery. The central optic is connected with the outer core by at least one spring haptic, thereby forming the intraocular lens that may be placed in the capsular bag of an eyeball. When the capsular bag of the eyeball is not complete, the two haptics connecting the outer core can fix in the ciliary sulcus of the eyeball, so that the intraocular lens may be positioned.

Accordingly, the position of the central optic of the intraocular lens in the eyeball may be adjusted so as to change the entire optical power of the eyeball. Thus, when the patient implanted with the intraocular lens of the present invention to have a far seeing, the central optic is located at the optimal position to have a far seeing. When the patient implanted with the intraocular lens of the present invention to look at the ground, the central optic of the intraocular lens may linearly displace forward through a determined distance automatically. When the patient implanted with the intraocular lens of the present invention to read a predetermined nearest distance, the central optic of the intraocular lens may be adjusted automatically to be located at the front stop position close to the anterior optic.

The power source of the intraocular lens of the present invention is the gravity. Thus, by change of the inclined angle of the user, or by variation of the external magnetic field, the push force that is exerted on the central optic of the intraocular lens may be regulated, so as to actively control the position of the central optic of the intraocular lens, so that the user may actively control and regulate the refractive power of the eyeball.

In accordance with one aspect of the present invention, there is provided an intraocular lens that may accommodate automatically, comprising: a central optic, an outer core, a stroke cylinder, an anterior optic, a posterior optic, at least one spring haptic, and a magnetic heavy part, wherein, the anterior optic at a front end of the central optic is connected with the stroke cylinder, the posterior optic at a rear end of the central optic is connected with the outer core, the outer core is connected with the stroke cylinder, thereby enclosing the central optic in an inner periphery, the central optic is connected with the outer core by at least one spring haptic, the intraocular lens may be placed in the capsular bag of an eyeball, a power source of the intraocular lens is the gravity, by change of an inclined angle of a user, a push force that is exerted on the central optic of the intraocular lens may be regulated, so as to actively control a position of the central optic, so that the user may actively control and regulate the refractive power of the eyeball.

Further benefits and advantages of the present invention will become apparent after a careful reading of the detailed description with appropriate reference to the accompanying drawings.

BRIEF DESCRIPTION OF THE DRAWINGS

FIG. 4 is a front plan view of an intraocular lens that may accommodate automatically in accordance with the present invention;

FIG. 5 is a side plan cross-sectional view of the intraocular lens that may accommodate automatically in accordance with the present invention;

FIG. 6 is a cross-sectional view of the intraocular lens of the present invention that is implanted in the eyeball;

FIG. 7 is a cross-sectional view of the intraocular lens of the present invention that is implanted in the eyeball;

FIGS. 12–21 are plan views of other embodiments of the intraocular lens that may accommodate automatically in accordance with the present invention; and FIGS. 22–24 are schematic views of an eyeglass frame with magnets and its interaction with the intraocular lens that may accommodate automatically in accordance with the present invention.

DETAILED DESCRIPTION OF THE INVENTION

Figure 1:
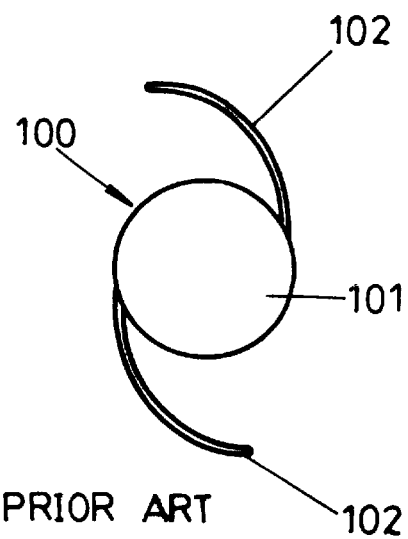
FIG. 1 is a plan view of a conventional intraocular lens in accordance with the prior art.
Figure 2:
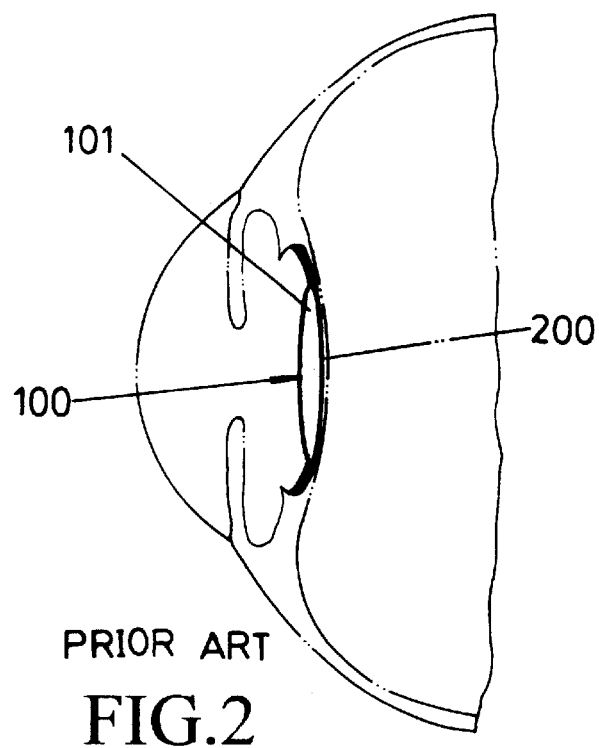
FIG. 2 is a plan view of a conventional intraocular lens that is mounted in the capsular bag.
Figure 3:
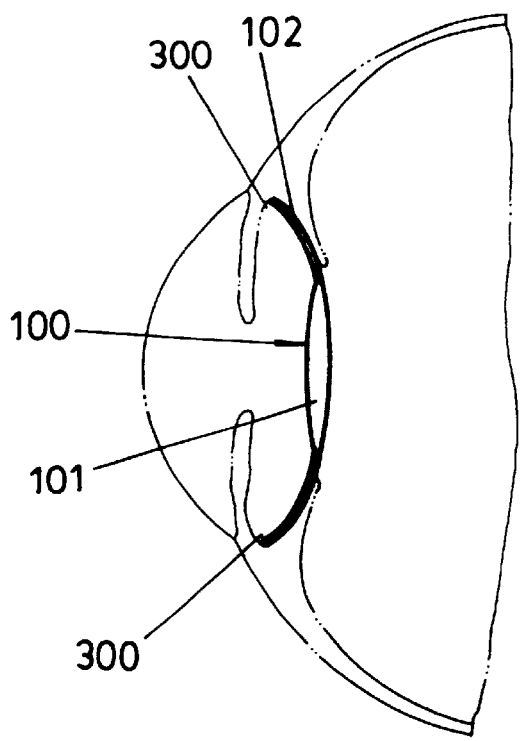
FIG. 3 is a plan view of a conventional intraocular lens that is mounted in the ciliary sulcus.

Referring to the drawings and initially to FIGS. 4 and 5, an intraocular lens that may accommodate automatically in accordance with the preferred embodiment of the present invention comprises a central optic 1, an outer core 2, a stroke cylinder 3, an anterior optic 4, a posterior optic 5, at least one spring haptic 6, a magnetic heavy part 7, and two haptics 8.

The front end of the central optic 1 is the anterior optic 4, and the rear end of the central optic 1 is the posterior optic 5 which is connected with the outer core 2 which is connected with the stroke cylinder 3 which is connected with the anterior optic 4, thereby enclosing the central optic 1 in the inner periphery. The magnetic heavy part 7 is located in the central optic 1 which is connected with the outer core 2 by at least one spring haptic 6. The top end and the bottom end of the outer side of the outer core 2 are respectively provided with a curved haptic 8.

Referring to FIG. 6, when the capsular bag 10 of the eyeball of the patient is complete, the two haptics 8 of the intraocular lens of the present invention retract inward into the capsular bag 10.

Referring to FIG. 7, when the capsular bag 10 of the eyeball of the patient is not complete, the intraocular lens can be fixed by the ciliary sulcus 20. The two haptics 8 of the intraocular lens of the present invention are supported in the ciliary sulcus 20 respectively, so that the intraocular lens may be positioned.

Figure 8:
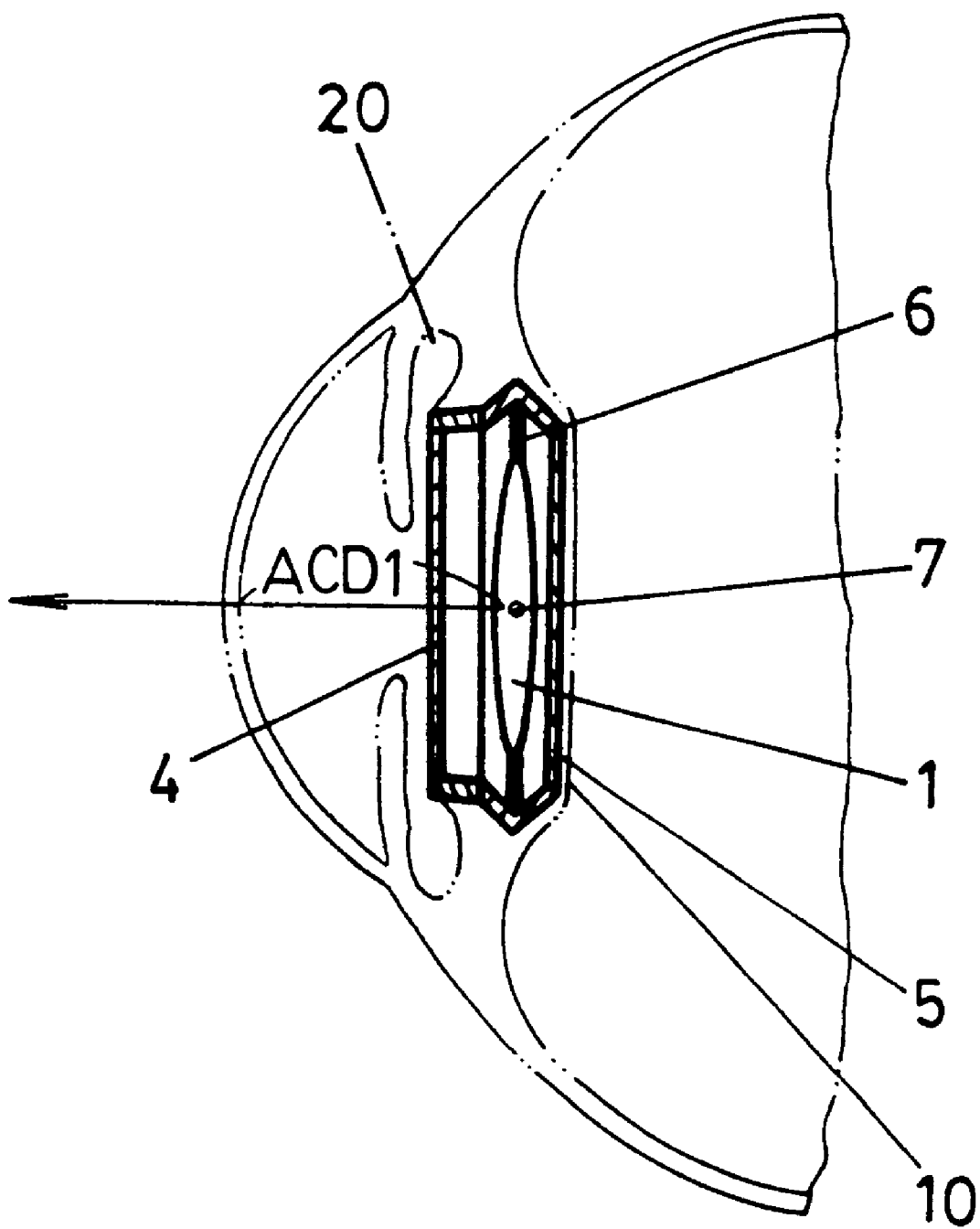
FIG. 8 is a schematic view of the intraocular lens of the present invention that has a far seeing.

Referring to FIG. 8, when the patient implanted with the intraocular lens of the present invention to have a far seeing, the anterior chamber distance ACD1 between the central optic of the intraocular lens and the cornea is the greatest. At this time, the intraocular lens is located at the optimal position to have a far seeing.

Figure 9:
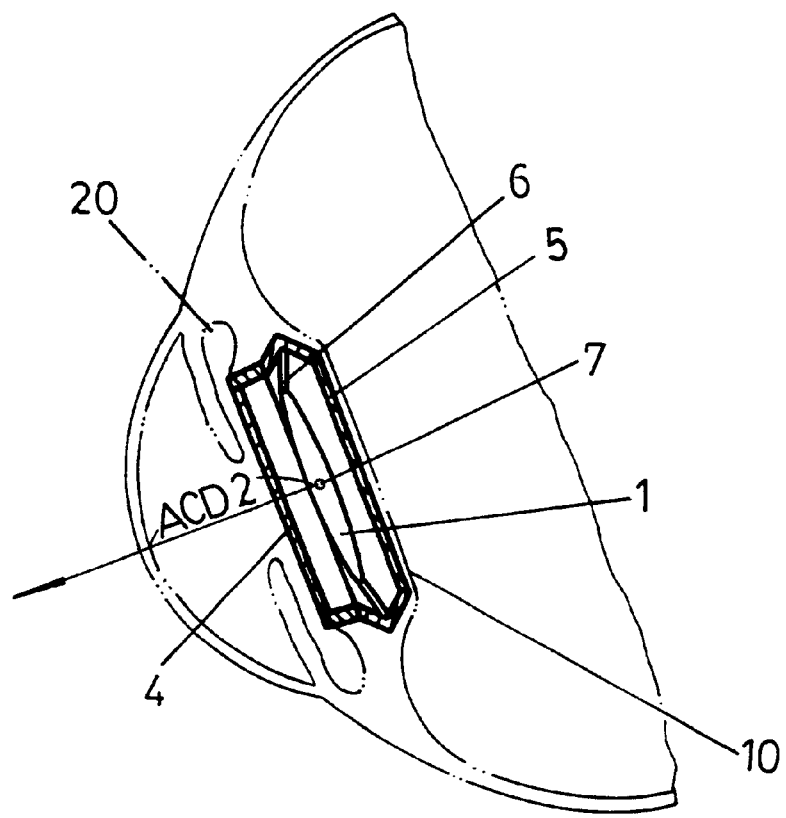
FIG. 9 is a schematic view of the intraocular lens of the present invention that is used for looking at the ground.
Figure 10:
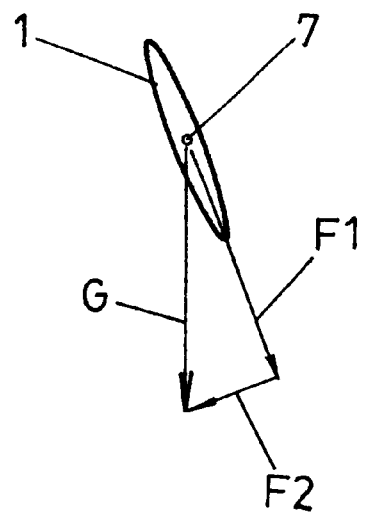
FIG. 10 is a schematic view of components of gravity exerted on the central optic of the intraocular lens of the present invention that is used for looking at the ground.

Referring to FIGS. 9 and 10, when the patient implanted with the intraocular lens of the present invention to look at the ground, the central optic 1 of the intraocular lens is subjected to action of the components F1 and F2 of the gravity "G" to linearly displace forward through a determined distance automatically as shown in FIG. 10, such that the anterior chamber distance ACD2 is smaller than the anterior chamber distance ACD1.

Figure 11:
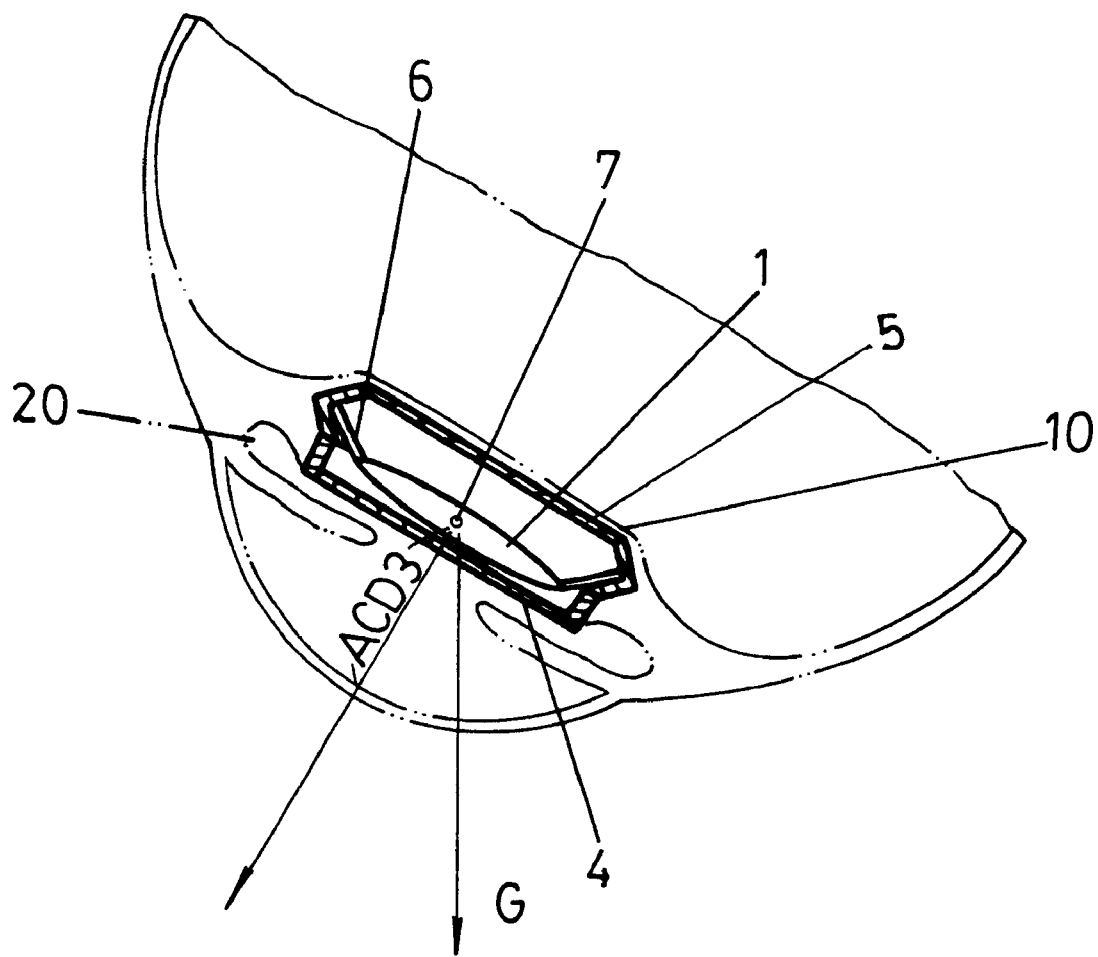
FIG. 11 is a schematic view of the intraocular lens of the present invention that is used for reading a book.

Referring to FIG. 11, when the patient implanted with the intraocular lens of the present invention to read a predetermined nearest distance, the central optic 1 of the intraocular lens may be adjusted automatically to be located at the front stop position close to the anterior optic 4, such that the anterior chamber distance ACD3 is the smallest. That is, ACD1>ACD2>ACD3.

The power source of the intraocular lens of the present invention is the gravity. By change of the inclined angle of the user, such as far seeing, looking at the ground or reading book, the push force that is exerted on the central optic of the intraocular lens may be regulated, so as to actively control the position of the central optic of the intraocular lens, so that the user may actively control and regulate the refractive power of the eyeball.

Referring to FIG. 12, in accordance with another embodiment of the present invention, the central optic 1' of the intraocular lens is fixed in the outer core 2 by one spring haptic or multiple spring haptics 6'. The outer periphery of the central optic 1' is cylindrical, and may slide along the stroke cylinder 3' that is like a cylinder wall to function like a cylinder and a piston. When the central optic 1' is displaced due to the gravity, the central optic 1' is guided by the inner wall of the stroke cylinder 3'.

Referring to FIG. 13, in accordance with a further embodiment of the present invention, the anterior optic of the intraocular lens is not defined.

Referring to FIG. 14, in accordance with a further embodiment of the present invention, the stroke cylinder of the intraocular lens is not defined.

Referring to FIG. 15, in accordance with a further embodiment of the present invention, the posterior optic of the intraocular lens is not defined.

Referring to FIG. 16, in accordance with a further embodiment of the present invention, the outer core is cut partially to present an opened curve.

Referring to FIG. 17, in accordance with a further embodiment of the present invention, the two sides of the outer core are opened.

Referring to FIG. 18, in accordance with a further embodiment of the present invention, the central optic 1" is separated from the outer core 2". The spring haptics 6" at the peripheral of the central optic 1" may be placed into and positioned in the grooves 21" of the outer core 2", they can be implanted into eyeball separately, while during the operation is performing.

Referring now to FIGS. 19 and 20, in accordance with a further embodiment of the present invention, the two haptics 8" of the intraocular lens are integrally formed with the central optic 1" by an injection molding process, thereby facilitating fabrication and assembly.

Referring to FIG. 21, in accordance with a further embodiment of the present invention, the stroke cylinder 3" of the intraocular lens may be separated from the other parts. For facilitating assembly during operation, after the central optic 1, the outer core 2, and the haptics 8 have been mounted into the capsular bag 10 of the eyeball of the patient, the modified stroke cylinder 3" may then be mounted in the posterior capsule bag 10 of the eyeball of the patient.

Figure 23:
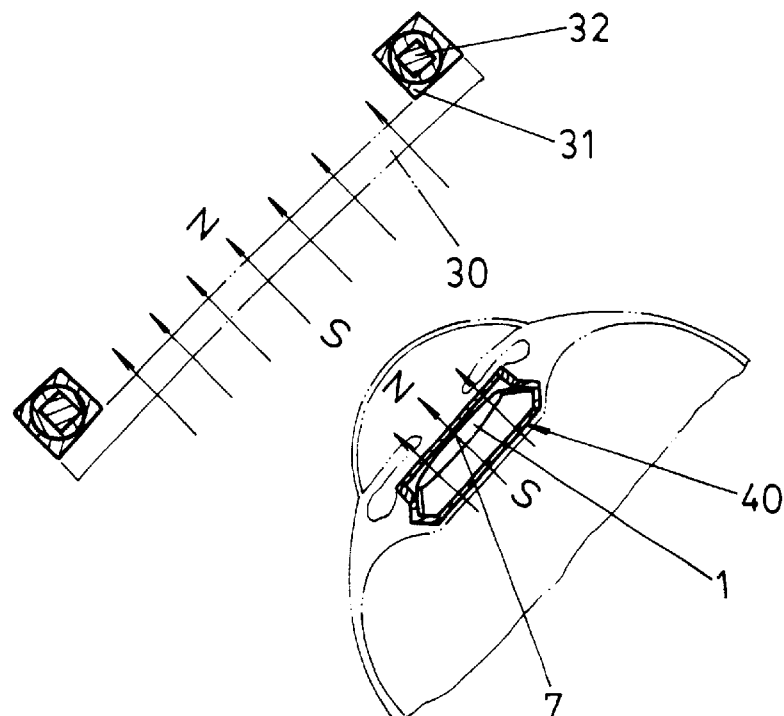
Figure 24:
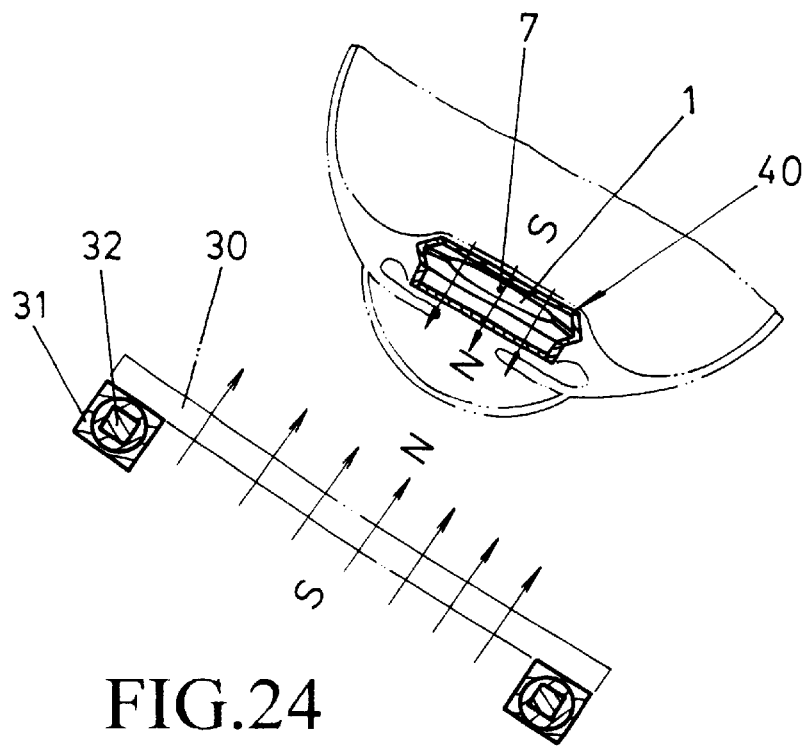

Referring to FIGS. 22–24, in accordance with a further embodiment of the present invention, when the position of the central optic of the intraocular lens needs to be adjusted, and when the central optic needs to resist the direction of the gravity, an external magnetic source may be used to resist the gravity, and may be used to drive the central optic of the intraocular lens to be positioned at the required position.

As shown in FIGS. 22 and 23, when the user raises his head to see a near object, the shaft 31 formed by the magnet 32 on the eyeglass frame 30 may mutually react with the magnetic heavy part 7 of the intraocular lens 40, so that the central optic 1 of intraocular lens 40 may be attracted to move forward by the magnetic field of the same direction, or be repelled to move rearward by the magnetic field of the opposite direction.

As shown in FIGS. 22 and 24, when the user lower his head to see a near object, the shaft 31 formed by the magnet 32 on the eyeglass frame 30 may mutually react with the magnetic heavy part 7 of the intraocular lens 40, so that the central optic 1 of the Intraocular lens 40 may be attracted to move forward by the magnetic field of the same direction, or be repelled to move rearward by the magnetic field of the opposite direction.

Therefore, the strength and direction of the external magnetic field may be adjusted, to control the position of the central optic of the intraocular lens.

Accordingly, in accordance with the intraocular lens that may accommodate automatically of the present invention, by change of the inclined angle of the user (such as far seeing, looking at the ground or reading book), or by variation of the external magnetic field, the push force that is exerted on the central optic of the intraocular lens may be regulated, so as to actively control the position of the central optic of the intraocular lens, so that the user may actively control and regulate the refractive power of the eyeball.

Although the invention has been explained in relation to its preferred embodiment as mentioned above, it is to be understood that many other possible modifications and variations can be made without departing from the scope of the present invention. It is, therefore, contemplated that the appended claim or claims will cover such modifications and variations that fall within the true scope of the invention.

What is claimed is:

1. An intraocular lens that may accommodate automatically, comprising: a central optic, an outer core, a stroke cylinder, an anterior optic, a posterior optic, at least one spring haptic, and a magnetic heavy part, wherein, the anterior optic at a front end of the intraocular lens is connected with the stroke cylinder, the posterior optic at a rear end of the intraocular lens is connected with the outer core, the outer core is connected with the stroke cylinder, thereby enclosing the central optic in an inner periphery, the central optic is connected with the outer core by at least one spring haptic, the intraocular lens is configured to be placed in a capsular bag of an eyeball and wherein, a power source of the intraocular lens is the gravity, by change of an inclined angle of a user wherein, a push force that is exerted on the central optic of the intraocular lens may be regulated, so as to actively control the position of the central optic of the intraocular lens, so that the user may actively control and regulate the refractive power of the eyeball that is implanted with the intraocular lens.

2. The intraocular lens that may accommodate automatically in accordance with claim 1, wherein the outer core of the intraocular lens has a top end and a bottom end respectively provided with a curved haptic, whereby when the capsular bag of the eyeball is not complete, the two haptics of the intraocular lens are fixed in a ciliary sulcus of the eyeball, so that the intraocular lens may be positioned.

3. The intraocular lens that may accommodate automatically in accordance with claim 1, wherein an outer periphery of the central optic is cylindrical, and slides along the stroke cylinder, so that when the central optic is displaced due to the gravity, the central optic is guided by the stroke cylinder.

4. The intraocular lens that may accommodate automatically in accordance with claim 1, wherein the anterior optic of the intraocular lens is not defined.

5. The intraocular lens that may accommodate automatically in accordance with claim 1, wherein the stroke cylinder of the intraocular lens is not defined.

6. The intraocular lens that may accommodate automatically in accordance with claim 1, wherein the posterior optic of the intraocular lens is not defined.

7. The intraocular lens that may accommodate automatically in accordance with claim 1, wherein the outer core is cut partially to present an opened curve.

8. The intraocular lens that may accommodate automatically in accordance with claim 1, wherein two sides of the outer core are opened.

9. The intraocular lens that may accommodate automatically in accordance with claim 1, wherein the central optic is separated from the outer core, whereby the spring haptics at the peripheral of the central optic are placed into and positioned in grooves of the outer core when during performing the operation.

10. The intraocular lens that may accommodate automatically in accordance with claim 1, wherein the stroke cylinder of the intraocular lens is separated from the outer core, so that the stroke cylinder is mounted into the capsular bag of the eyeball individually.

11. The intraocular lens that may accommodate automatically in accordance with claim 1, wherein the haptics of the intraocular lens are integrally formed with the central optic.

12. The intraocular lens that may accommodate automatically in accordance with claim 1, wherein an external magnetic force may mutually react with the magnetic heavy part, such that the central optic of the intraocular lens may be attracted to move forward by the magnetic field of the same direction, or be repelled to move rearward by the magnetic field of the opposite direction.

13. The Intraocular lens that may accommodate automatically in accordance with claim 1, wherein the number of the magnetic heavy part may be zero or one or more than one.

* * * * *